(12) United States Patent
Bassin et al.

(10) Patent No.: US 10,105,506 B2
(45) Date of Patent: Oct. 23, 2018

(54) SETUP AUTOMATION FOR RESPIRATORY TREATMENT APPARATUS

(75) Inventors: David John Bassin, Coogee (AU); Glenn Richards, Clevedon (NZ)

(73) Assignee: ResMed Limited (AU)

( * ) Notice: Subject to any disclaimer, the term of this patent is extended or adjusted under 35 U.S.C. 154(b) by 1049 days.

(21) Appl. No.: 13/383,320

(22) PCT Filed: Apr. 7, 2010

(86) PCT No.: PCT/AU2010/000393
§ 371 (c)(1),
(2), (4) Date: Jan. 10, 2012

(87) PCT Pub. No.: WO2011/006184
PCT Pub. Date: Jan. 20, 2011

(65) Prior Publication Data
US 2012/0145153 A1    Jun. 14, 2012

Related U.S. Application Data

(60) Provisional application No. 61/225,327, filed on Jul. 14, 2009.

(51) Int. Cl.
*A61M 16/00* (2006.01)

(52) U.S. Cl.
CPC ...... *A61M 16/0069* (2014.02); *A61M 16/024* (2017.08); *A61M 2016/0021* (2013.01);
(Continued)

(58) Field of Classification Search
CPC .............. A61M 16/00; A61M 16/0051; A61M 2016/0021; A61M 16/0069;
(Continued)

(56) References Cited

U.S. PATENT DOCUMENTS

| | | | | |
|---|---|---|---|---|
| 5,458,137 A | * | 10/1995 | Axe et al. | 128/204.23 |
| 6,000,396 A | * | 12/1999 | Melker et al. | 128/204.21 |

(Continued)

FOREIGN PATENT DOCUMENTS

| | | | | |
|---|---|---|---|---|
| EP | 0753320 A1 | | 1/1997 | |
| WO | WO 96/11717 | * | 7/1995 | ............ A61M 16/00 |

(Continued)

OTHER PUBLICATIONS

International Search Report and Written Opinion, PCT/AU10/00393, dated Aug. 6, 2010.

(Continued)

*Primary Examiner* — Gregory Anderson
*Assistant Examiner* — Elliot S Ruddie
(74) *Attorney, Agent, or Firm* — Lerner, David, Littenberg, Krumholz & Mentlik, LLP

(57) ABSTRACT

A respiratory treatment apparatus implements pressure delivery control settings by improved set-up procedures. In such an embodiment, a processor may automate setting of parameters for delivering a controlled flow of breathable gas. Data sets of pressure delivery parameter settings may be associated with one or more respiratory pathology indicators. The respiratory pathology indicators may each represent a different respiratory condition diagnosis. The processor may then prompt for an input of at least one of the respiratory pathology indicators. In response to the input, a particular set of pressure delivery parameter settings associated with the input respiratory pathology indicator may then serve as a basis for setting controls for delivering a controlled flow of breathable gas for respiratory treatment.

33 Claims, 5 Drawing Sheets

(52) U.S. Cl.
CPC ............ *A61M 2016/0027* (2013.01); *A61M 2205/505* (2013.01)

(58) Field of Classification Search
CPC ........ A61M 2205/50; A61M 2205/502; A61M 2205/505; A61M 2016/0027; A62B 9/00; A62B 9/02
USPC ................ 128/204.21, 204.23; 715/705, 707
See application file for complete search history.

(56) References Cited

U.S. PATENT DOCUMENTS

| | | | |
|---|---|---|---|
| 6,148,814 A | | 11/2000 | Clemmer et al. |
| 6,530,372 B1* | | 3/2003 | Madaus et al. .......... 128/204.23 |
| 6,575,163 B1* | | 6/2003 | Berthon-Jones ......... 128/204.18 |
| 2001/0004893 A1 | | 6/2001 | Biondi et al. |
| 2003/0111078 A1* | | 6/2003 | Habashi ................... 128/204.18 |
| 2007/0000494 A1 | | 1/2007 | Banner et al. |
| 2008/0072902 A1* | | 3/2008 | Setzer et al. ............. 128/204.21 |
| 2008/0078390 A1 | | 4/2008 | Milne et al. |
| 2010/0275921 A1* | | 11/2010 | Schindhelm et al. ... 128/204.23 |

FOREIGN PATENT DOCUMENTS

| | | | | |
|---|---|---|---|---|
| WO | 2004020030 A1 | | 3/2004 | |
| WO | WO 2004/020030 | * | 3/2004 | ............ A61M 16/00 |
| WO | 2005/063323 A1 | | 7/2005 | |
| WO | 2008/138040 A1 | | 11/2008 | |
| WO | 2008/145632 A2 | | 12/2008 | |
| WO | 2008148134 A1 | | 12/2008 | |
| WO | 2009059359 A1 | | 5/2009 | |

OTHER PUBLICATIONS

White, D.P., "A look toward the future", Clinics in Chest Medicine, Mar. 1998, 19(1), pp. 219-221.
Extended European Search Report for Application No. 10799267.9 dated Aug. 7, 2014.

* cited by examiner

| | Obstructive Disorder | Restrictive Disorder | OHS | Normal |
|---|---|---|---|---|
| Rise Time Default | 150ms | 300ms | 200ms | 200ms |
| Fall Time Default | 100ms | 400ms | 200ms | 200ms |
| Ti/Tot Ratio | 0.3 | 0.4 | 0.4 | 0.4 |
| Cycling Sensitivity | High | Low | Med | Med |
| Trigger Sensitivity | Med | Med | Med | Med |
| EPAP (cm $H_2O$) | 4 | 4 | 6 | 4 |
| PS (cm $H_2O$) | 6 | 6 | 8 | 6 |
| Min PS (cm $H_2O$) | 4 | 4 | 4 | 4 |
| Max PS (cm $H_2O$) | 15 | 15 | 15 | 15 |

Fig. 3

SETUP AUTOMATION FOR RESPIRATORY TREATMENT APPARATUS

CROSS-REFERENCE TO RELATED APPLICATIONS

The present application is a national phase entry under 35 U.S.C. § 371 of International Application No. PCT/AU2010/000393 filed Apr. 7, 2010, published in English, which claims priority from U.S. Provisional Patent Application No. 61/225,327 filed Jul. 14, 2009. The disclosures of said applications are incorporated by reference herein.

FIELD OF THE TECHNOLOGY

The present technology relates to respiratory treatment apparatus used in therapeutic applications. More particularly, it relates to automated set-up procedures for such devices.

BACKGROUND OF THE TECHNOLOGY

Typically a respiratory treatment apparatus can provide a patient with a supply of breathable gas (usually air, with or without supplemental oxygen) at a therapeutic pressure or pressures, at appropriate times during the subject's breathing cycle. Such therapies may include continuous positive airway pressure (CPAP), nasal intermittent positive pressure ventilation (NIPPV) and variable positive airway pressure (VPAP), for example. The therapy may be used for treatment of various respiratory conditions including, for example, Chronic Obstructive Pulmonary Disease ("COPD"), sleep disordered breathing (SDB), obstructive sleep apnea (OSA), etc.

Pressure related settings of a respiratory treatment apparatus can be determined by a clinician by monitoring a patient's respiration during a titration session. For example, the goal of a CPAP titration session is to determine what level of CPAP treatment is needed to abolish a patient's upper-airway irregularities. Throughout such a session, a physician or clinician may manually adjust a CPAP level (pressure) to resolve observed respiratory irregularities. In some devices, a clinician may also manually adjust settings for controlling the triggering and cycling parameters that relate to the detection of patient respiration and used for patient ventilator synchronization.

In some respiratory treatment apparatus, automated control may be implemented so that the device may even adjust treatment pressure settings during treatment in response to detected sleep disordered breathing events during treatment. For example, upon detecting an occurrence of an obstructive apnea, the device might increase the CPAP pressure by some increment until the occurrence is no longer detected. Such a device may be considered an auto-titration CPAP device.

Nevertheless, even in such devices, initial pressure treatment settings are typically set by a clinician or physician. There may be a need to improve the automated systems of respiratory treatment apparatus so as to promote efficient and effective set up of the control parameters used to control pressure therapy.

BRIEF SUMMARY OF THE TECHNOLOGY

In an aspect of the present technology, an apparatus, such as a respiratory treatment apparatus, implements pressure delivery control settings by improved set-up procedures.

In another aspect of the technology, a method involves control by a processor to automate setting of parameters for delivering a controlled flow of breathable gas. The method may include associating one or more arrays or sets of pressure delivery parameter settings with one or more respiratory pathology indicators. Each respiratory pathology indicator may represent a different respiratory condition diagnosis. The method may prompt for an input of at least one of the respiratory pathology indicators. The method may then receive input associated with a particular one of the respiratory pathology indicators. In response to the input, the method may then select the array or set of pressure delivery parameter settings associated with the particular one of the respiratory pathology indicators for setting a processor to deliver a controlled flow of breathable gas.

In some embodiments, a respiratory condition diagnosis of a respiratory pathology indicator may represent an obstructive disorder, a restrictive disorder, a Chronic Obstructive Pulmonary Disease and/or an obesity hypoventilation syndrome.

In some embodiments, an array or set of pressure delivery parameter settings may include one, two or more of a rise time setting, an inspiratory time to respiration cycle time ratio setting (e.g., a setting for the maximum ratio of inspiratory time to a total breath duration), a cycling sensitivity setting, a trigger sensitivity setting, a positive end expiratory pressure setting, an expiratory positive airway pressure setting, a pressure support setting, a maximum pressure support setting and a minimum pressure support setting.

The array or set of pressure delivery parameter settings may be initial settings that are modifiable by further operation of the processor.

In some embodiments, the method may further prompt for input of classification data or information concerning the respiratory condition diagnosis of the particular one of the respiratory pathology indicators. The classification information may represent degrees of severity where each degree of severity may be associated with at least one different setting for at least one common pressure delivery parameter. In some cases, the degrees of severity may represent mild, moderate and severe obstructive disorder classifications.

In still further embodiments, the method may involve prompting for input of a measured quantification concerning the respiratory condition diagnosis of a selected or particular one of the respiratory pathology indicators. The measured quantification may, for example, be a quantification of a sniff nasal pressure. In such as case, a trigger sensitivity setting may be set as a function of the input sniff nasal pressure. In some embodiments, the measured quantification may be a height and weight or a body mass index. In such a case, an expiratory positive airway pressure setting may be set as a function of the input height and weight or the input body mass index.

In still further embodiments, the method may involve delivering a controlled flow of breathable gas according to the set of pressure delivery parameter settings associated with the selected or particular one of the respiratory pathology indicators.

In some embodiments, the method may further include prompting for a manual adjustment to the set of pressure delivery parameter settings associated with the selected one of the respiratory pathology indicators.

Some embodiments of the present technology may also include an automated parameter-setting respiratory treatment apparatus for delivering a controlled flow of breathable gas. The apparatus may include a controller having at least one processor to access data representing an association between an array or set of pressure delivery parameter settings and at least one respiratory pathology indicator that represents a respiratory condition diagnosis. The controller may be further configured to prompt for an input of the at least one respiratory pathology indicator. The controller may be further configured to receive input associated with the at least one respiratory pathology indicator. The controller may be further configured, in response to the input, to select the set or array of pressure delivery parameter settings associated with the particular one of the respiratory pathology indicators to set a controlled flow of breathable gas. Optionally, the apparatus, controller or processor may be further configured with any or all of the features of the methods previously discussed.

In some embodiments, the apparatus may further include a flow generator controlled by the controller. The controller may then be further configured to deliver a controlled flow of breathable gas with the flow generator according to the array or set of pressure delivery parameter settings associated with the particular one of the respiratory pathology indicator. Optionally, the controller may also be further configured to prompt for a manual adjustment to the array or set of pressure delivery parameter settings associated with the particular one of the respiratory pathology indicators.

Some embodiments of the technology may involve a system for automated parameter-setting of a respiratory treatment apparatus for delivering a controlled flow of breathable gas. The system may include an apparatus as previously described. In some embodiments the system may include a means for associating arrays or sets of pressure delivery parameter settings with a plurality of respiratory pathology indicators where each respiratory pathology indicator represents a different respiratory condition diagnosis. The system may also include a means for prompting for an input of at least one of the respiratory pathology indicators. The system may also include a means for receiving input associated with a particular one of the respiratory pathology indicators. The system may also include a means for selecting in response to the input, the set or array of pressure delivery parameter settings associated with the particular one of the respiratory pathology indicators for setting a respiratory treatment apparatus to deliver a controlled flow of breathable gas. Still further, the system may include a flow generation means for generating a flow of breathable gas based on the array or set of pressure delivery parameter settings associated with the particular one of the respiratory pathology indicators. In some embodiments, the system may also include a means for manual adjustment to the array or set of pressure delivery parameter settings associated with the particular one of the respiratory pathology indicators.

Further embodiments and features of the technology may be apparent from the following detailed disclosure, claims and drawings.

BRIEF DESCRIPTION OF THE DRAWINGS

The present technology is illustrated by way of example, and not by way of limitation, in the figures of the accompanying drawings, in which like reference numerals refer to similar elements including:

FIG. 3 is a table illustrating associations between sets of pressure treatment control parameter settings and disease types;

DETAILED DESCRIPTION

Figure 1:
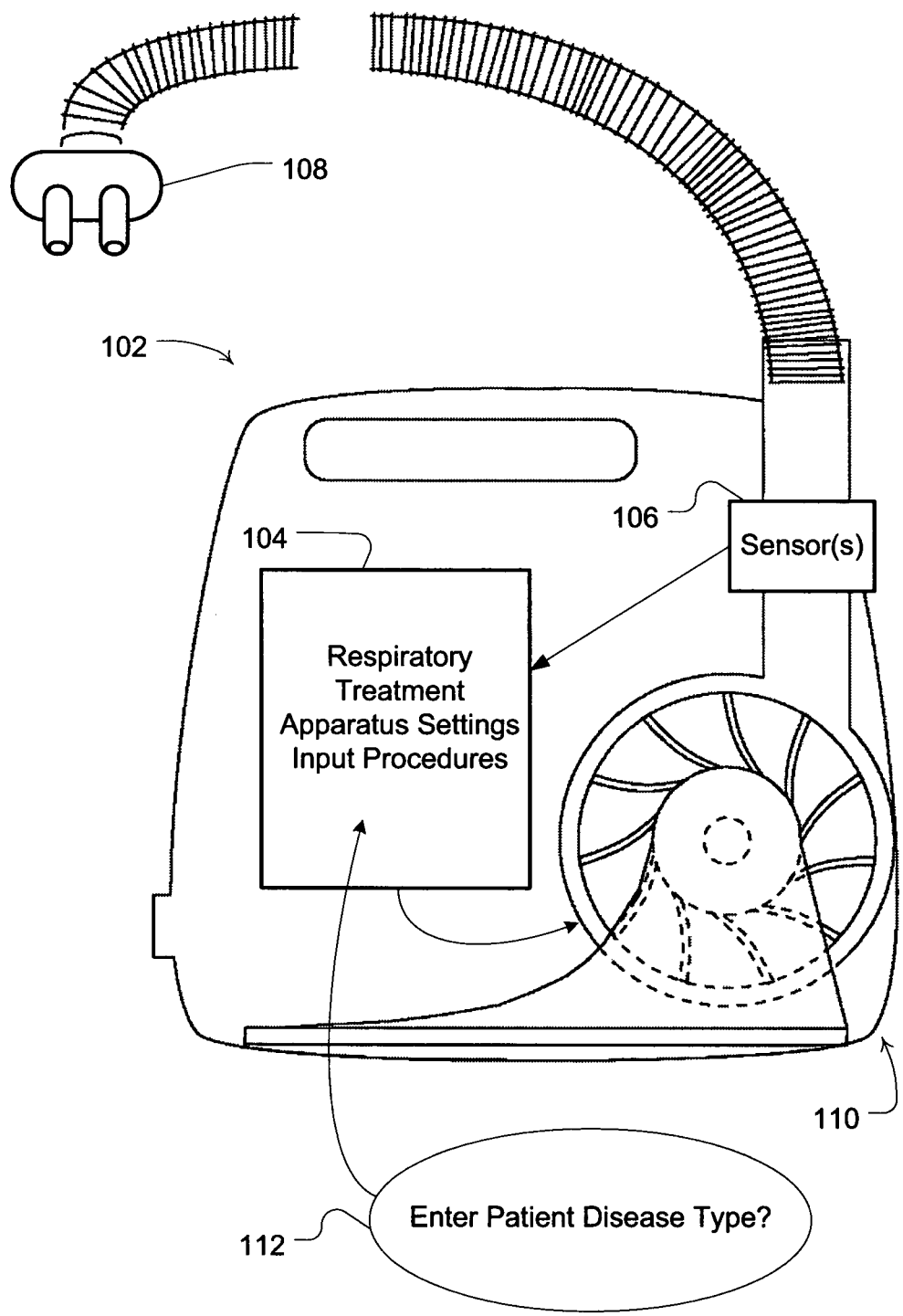
FIG. 1 shows an illustration of an example respiratory treatment device configured with an automated disease-type settings selection procedure of the present technology.

As illustrated in FIG. 1, embodiments of the present technology may include a respiratory treatment apparatus 102 with disease-based set-up procedures for selection of pressure delivery control parameter settings. In such an example, the apparatus 102 will include a controller 104 that may have one or more processors to implement the particular set-up procedures, methodologies and algorithms as described in more detail herein. Thus, the controller may be implemented with integrated chips, a memory and/or other control instruction, data or information storage medium. For example, programmed instructions encompassing such set-up methodologies may be coded on integrated chips in the memory of the device or apparatus to form an application specific integrated chip (ASIC). Such instructions may also or alternatively be loaded as software or firmware using an appropriate data storage medium in which they reside to then control one or more programmable processors.

In the illustrated embodiment of FIG. 1, the controller 104 is configured with an automated set-up procedure that has access to data, such as a table data structure, representing settings or default settings for pressure control parameters. As discussed in more detail herein, the pressure delivery parameters are used in the control of the operation of a flow generator 110 to deliver pressure treatment to a patient via a patient interface such as a mask or cannula 108. A user or clinician may select settings for the various control parameters through utilization of a disease type selection user interface 112 capable of setting the operation of the respiratory treatment apparatus 102. Thus, the selection of a disease type or factors indicative thereof may be linked to the automated entry of particular settings for the pressure control parameters of the respiratory treatment apparatus. The entered settings associated with the selected disease type may then be used by the controller 104 to control the flow generator 110 to deliver a particular pressure therapy to a patient.

Figure 2:
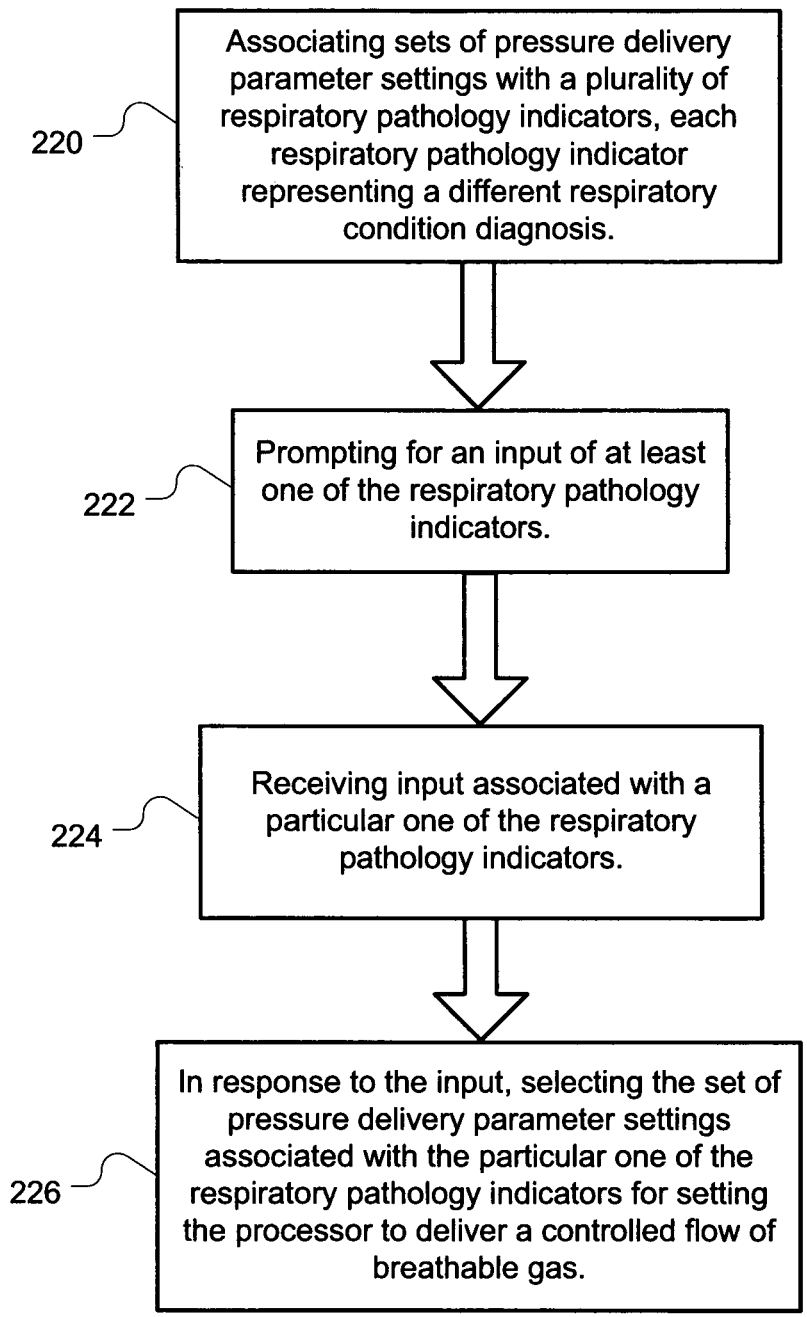
FIG. 2 illustrates an example embodiment of a control methodology for an apparatus of the present technology.

Example steps of a methodology of the present technology are further illustrated in the flow chart of FIG. 2. At 220, arrays or sets of pressure delivery parameter settings are associated with a plurality of respiratory pathology indicators. Each respiratory pathology indicator may be a designator for or represent a different respiratory condition diagnosis. For example, the respiratory pathology indicators may represent classifications for sleep disordered breathing patients (e.g., obstructive disorder, restricted disorder, etc.) or other respiratory disease patients (e.g., chronic obstructive pulmonary disease, etc.) As discussed in more detail herein, a set of pressure delivery parameter settings may be one or more setting values for one or more parameters used in the control of pressure treatment (e.g., a pressure support level, an expiratory positive airway pressure level, a cycle threshold, trigger threshold, etc.) This information and their associations may be stored as data in one or more data structures, such as a table, of a memory accessible by a controller or programmed processor as previously discussed.

Figure 4:
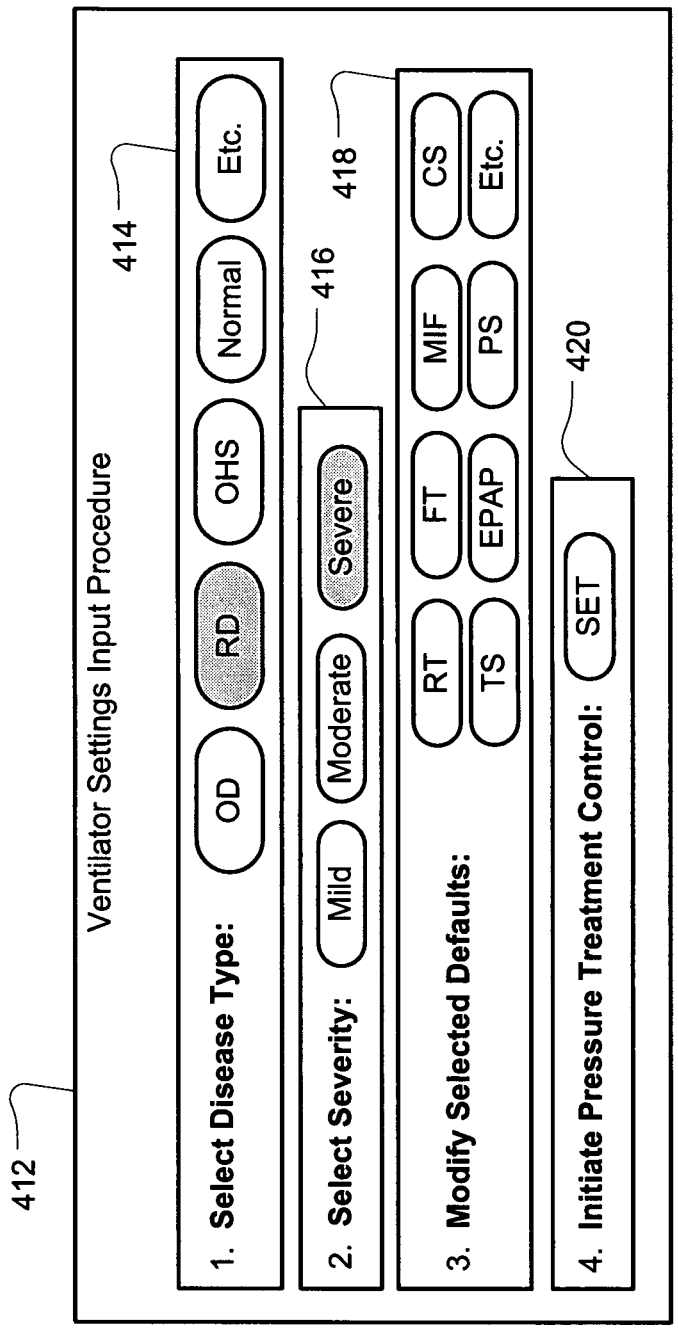
FIG. 4 is an illustration of an example graphic user interface for automated parameter setting according to an embodiment of the present technology.

At 222, an apparatus or processor may prompt for an input of at least one of the respiratory pathology indicators. For example, such prompting may be implemented by a user interface such as a GUI of a display (e.g., LCD) or touch screen display. Still optionally, the interface may be implemented with other input components (e.g., mouse, keypad, function specific buttons, etc.) An example GUI embodiment is illustrated in FIG. 4 and discussed in more detail herein. At 224, the apparatus or processor receives the input associated with a particular one of the respiratory pathology indicators. At 226, based on the input, the apparatus or processor selects the array or set of pressure delivery parameter settings associated with the particular one of the respiratory pathology indicators. The apparatus or processor may then use the selected data as settings for delivering a controlled flow of breathable gas.

An example embodiment of the technology may be considered with regard to the table data structure shown in FIG. 3. It will be understood that while particular parameters, settings and disease conditions are illustrated, others may also or alternatively be implemented.

When implemented by a processor, data representing the information of the table of FIG. 3 may serve as a unique tool that allows some of the settings of the control of a flow generator to be optimised for different respiratory conditions. For example, an interface may ask a user to pick a type of disease such as the respiratory pathology indicators 320A, 320B, 320C, 320D with graphic icons or text labels. The interface logic may then select a set of settings 321 from a larger group of potential settings so as to optimise pressure delivery parameters 322A, 322B, 322B, 322C, 322D, 322E, 322F, 322G, 322G, 322H, 322I for the particular disease of the patient. For example, suitable settings for comfort-based pressure delivery parameters (e.g., Positive End Expiratory Pressure (PEEP), Expiratory Positive Airway Pressure (EPAP), Rise time, fall time, etc.), synchrony-based pressure delivery parameters (e.g., cycle sensitivity, trigger sensitivity, inspiratory time ratio etc.) and/or therapy-based pressure delivery parameters (e.g., pressure support, minimum pressure support and maximum pressure support, etc.) may be selected based on the determined pathology indicator.

In this embodiment, respiratory failure disorders intended for treatment by the respiratory treatment apparatus have been divided into three categories depending on their effect on lung mechanics. The designated categories include obstructive, normal, restrictive and obesity hypoventilation syndrome. Each of these categories leads to a different breathing pattern meaning that comfort and synchrony are optimal at different ventilator settings.

Obstructive diseases, such as COPD are typically characterised by rapid inspiration and very prolonged expiration. Restrictive diseases such as chest wall abnormalities are characterised by rapid shallow breathing. Normal mechanics are seen in central hypoventilation syndromes and neuromuscular diseases without scoliosis or chest wall deformities, and these patients have a relatively normal breathing pattern. Thus, particular settings may be implemented by data structures to suit such characterizations.

For example, patients with severe obstructive lung diseases may generally prefer rapid rise and fall times for comfort. Since they have prolonged expiration, synchrony may be optimized with ventilator settings that lead to shorter inspiratory times (e.g., a ratio of inspiratory time to total cycle time "Ti/Ttot"), and rapid cycling from inspiration to expiration.

Patients with severe restrictive lung disease have rapid respiratory and flow rates and may find longer rise and fall times more comfortable. Reduced cycling sensitivity assists in achieving adequate tidal volume.

The normal settings in the example are chosen to be intermediate and may be typical ventilator settings.

In some embodiments, a default group of settings may be implemented in the absence of a user selection of a particular respiratory pathology indicator. For example, the default set of settings may be the "normal" designated set of settings illustrated in FIG. 3.

As illustrated in FIG. 3 one or more parameters may be utilized to control the pressure delivery and their setting values or settings may be associated with various respiratory pathology indicators. For example, a setting for a rise time parameter 322A may be implemented. This parameter may control the time by which a measure of pressure delivered by the apparatus 102 changes from an expiratory positive airway pressure level (EPAP) to an inspiratory positive airway pressure level (IPAP) from the time that the apparatus is triggered into an inspiratory phase.

Similarly, a setting for a fall time parameter 322B may also be implemented. This parameter may control the time by which a measure of pressure delivered by the apparatus 102 changes from an IPAP level to an EPAP level from the time that the apparatus is cycled into an expiratory phase.

Another such parameter may be an inspiratory time ratio 322C (TiTot) which may be a ratio of the time of the inspiratory phase to a total time for a respiratory cycle. In other words, it may be a setting for the maximum ratio of inspiratory time to a total breath duration. Settings for this parameter may control the switching of the apparatus to the expiratory phase to deliver the EPAP level in the event that expiration is not detected (e.g., failure of a cycling threshold detection.)

Another example parameter may be a cycling sensitivity 322D. A setting for this parameter may adjust the threshold compared to a flow signal to detect whether a patient has initiated expiration so that the apparatus can respond by delivering an EPAP level.

A still further example parameter may be a trigger sensitivity 322E. A setting for this parameter may adjust the threshold compared to a flow signal to detect whether a patient has initiated inspiration so that the apparatus can respond by delivering the IPAP level.

Another such parameter may be an EPAP level 322F. A setting for this parameter may control the level or amount of pressure delivered during patient expiration. Such a measure may also be considered a PEEP level.

A still further parameter may be a pressure support ("PS") parameter 322G. A setting for this parameter may control the pressure delivered during inspiration. For example, an IPAP level may be determined as a function of the PS level and the EPAP level (e.g., PS=IPAP−EPAP).

In some embodiments, the PS level may be automatically adjusted (e.g., incremented or decremented) by the apparatus upon detection of or an absence of SDB events such as obstruction, flow limitation or flow flattening, etc. In such a case, additional pressure delivery parameters may include a minimum PS 322H and a maximum PS 322I. Settings for these parameters serve as a limit to such automatic changes made to the PS level.

Additional settings for other pressure control parameters may also be implemented and associated with one or more respiratory pathology indicators depending on the type of respiratory treatment apparatus. Nevertheless, through the association of different respiratory pathology indicators, different settings for a common parameter or different parameters may be suggested for use by the apparatus. In so doing, settings may be pre-configured so as to be particularly suitable for different patient respiratory condition diagnoses.

In some embodiments, additional prompting for user input by the apparatus may be implemented for further selection of suitable settings. For example, within one or more of the disease categories, sub-queries may allow finer adjustment of initial settings by further classifying the disease. Such questions when and if prompted may depend on the particular respiratory pathology indicator. For example, a general question may be asked for any disease state based on severity, such as by prompting for a rating as a number between 0 (normal) and 10 (worst possible severity). Optionally, this may be accomplished by inputting a traditional medical category such as that of mild, moderate and severe. In some embodiments, such questions may optionally be combined with the particular respiratory pathology indicator input query according to disease as well as severity (e.g., Severe Restrictive, Moderate Restrictive, Mild Restrictive etc.)

By way of further example, in those patients in the "Obstructive Disorder" category, a cycling threshold parameter (e.g., a proportion of inspiratory flow at which cycling into expiration occurs) might be set according to a further prompt requesting input of severity information. The input may then utilize the following example table data structure upon input of a severity designator so as to select a particular setting.

| | |
|---|---|
| Mild | 35% (cycle Threshold) |
| Moderate | 45% (cycle Threshold) |
| Severe | 55% (cycle Threshold) |

Similarly, other settings for different pressure delivery parameters may also be selected in this manner. For example, upon input of a "severe" severity indicator, a trigger sensitivity parameter may be set to a higher or different setting value compared to that of a mild or moderate severity designation.

In some embodiments, prompts for user input about a patient's symptoms may further control the selection of settings. For example, in "Obstructive Disorder" designated patients, the set-up procedures may prompt for information concerning whether the patient has expiratory flow limitation and to what degree. In response to an affirmative and/or severity-based user input through the user interface, different settings may be implemented. For example, an input affirmation by a user of a severe degree of flow limitation may implement a higher EPAP setting value being selected in the set of pressure delivery parameter settings proposed for treatment or for initiation of treatment.

In still further embodiments, the set-up procedures may prompt a user for objectively measurable quantities. In response to the user input of such quantities via the user interface, the automated selection of different settings may then be implemented. For example, in a neuromuscular patient category or pathology indicator, the maximal inspiratory pressure or the sniff nasal pressure may be requested through the user interface. In response to the input and based thereon, the apparatus may then adjust or select a particular trigger sensitivity associated with the particular quantity. For example, lower nasal pressure quantities may be associated with greater sensitivity setting values.

By way of further example, in an obesity hypoventilation syndrome patient category or pathology indicator, the user interface may prompt for the input of height and weight. The apparatus may then apply this data to calculate a body mass index (BMI). Alternatively, the apparatus may prompt for the input of a BMI. With the prompted or calculated BMI, different pressure delivery parameter settings may then be chosen. For example, higher BMI quantities may be associated with higher EPAP setting values.

In still further embodiments, the set-up procedures may implement a user interface to prompt a user or clinician to input patient characteristic data such as age, weight, height, general health questions and/or symptoms. The automated set-up procedures may then select an respiratory pathology indicator associated with the input data or prompt for user confirmation of one or more respiratory pathology indicators via the user interface based on the input data. In this way, the user interface may designate or classify the patient by selecting one or more potential respiratory pathology indicators from a larger group of potential respiratory pathology indicators. In so doing, an automated selection of a suitable set of pressure delivery parameter settings may then be chosen based on a particular respiratory pathology indicator suggested by the apparatus and confirmed by the user or clinician.

Example User Interface

An example graphic user interface 412 for a set-up procedure of the present technology is illustrated in FIG. 4. In the example, graphic icons may optionally be implemented to prompt for user input. For example, in the implemented version a disease type may be selected via prompted icons at 414 designated "OD", "RD", "OHS" or by some other designations. User or clinician input associated with these icons may represent a selection of "obstructive disorder", "restrictive disorder" and "obesity hypoventilation syndrome" respectively. User input may be by mouse, touch screen, arrow keys, buttons, voice activation or any other input device.

Upon input of the disease type, the user may optionally be prompted for input concerning pathology classification or severity with severity icons at 416. This prompting may optionally depend on a prior input of the disease type. For example, some pathology indicator selections may not include subsequent severity prompts and some may utilize different severity prompts from others.

This input data may then be utilized by the apparatus to select a set of parameter settings based on pre-configured associations between the input, settings, parameters and/or pathology indicators.

At 418, the values for a set of one or more of the selected parameter settings may then optionally be modified by a user by prompting the user. In the example at 418, icons may designate different ones of the parameters previously described. User or clinician input may then be provided to optionally adjust each setting of each parameter if desired.

At 420, the apparatus may prompt the user to start the apparatus so as to deliver pressure treatment based on the selected set of pressure delivery parameter settings or the modified versions thereof that were adjusted at 418.

Example Controller Architecture

Figure 5:
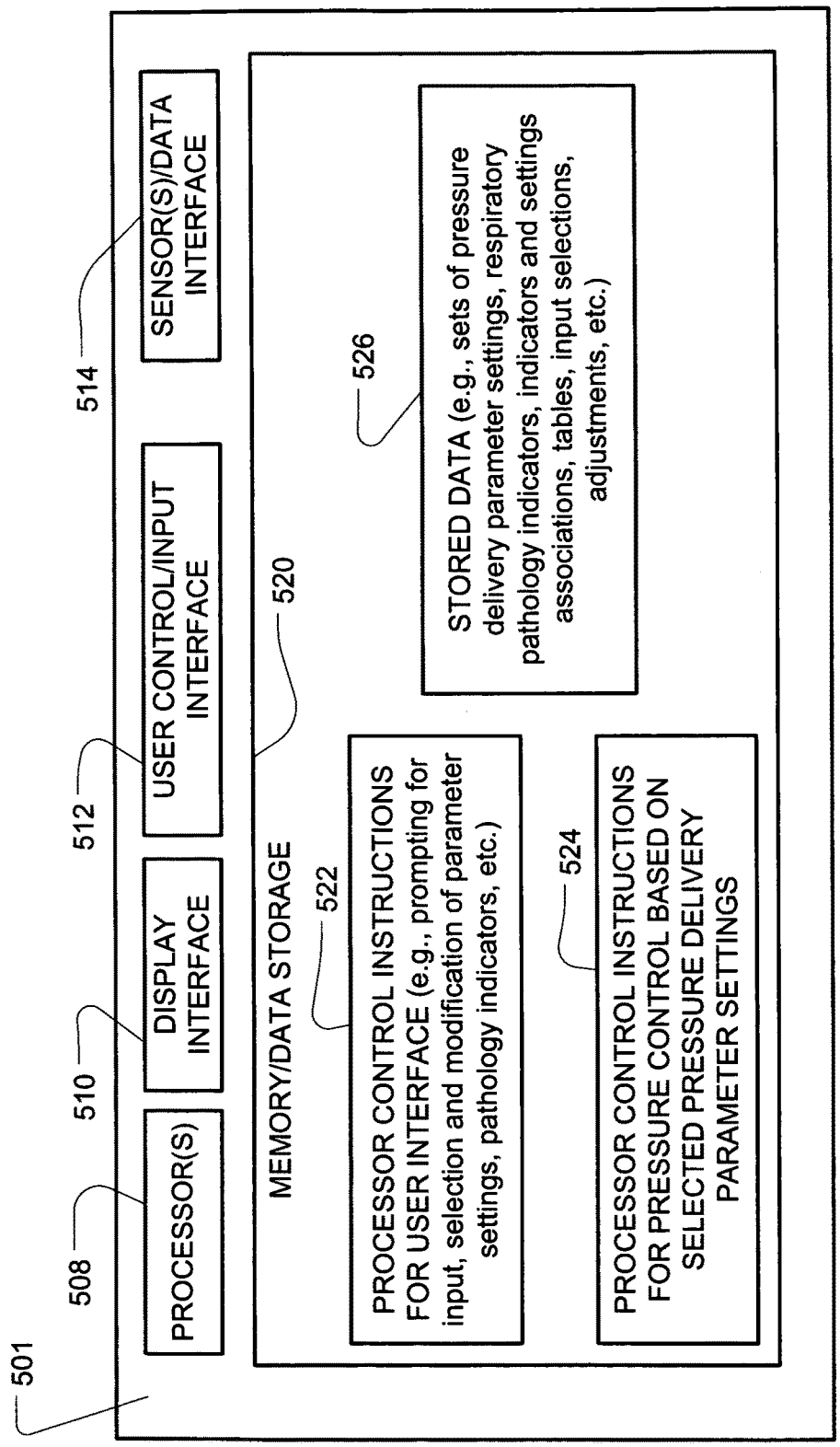
FIG. 5 is a block diagram of a controller for a respiratory treatment apparatus including example components thereof suitable for implementing the methodologies of the present technology.

An example system architecture of a set-up controller 501 is illustrated in the block diagram of FIG. 5. In the illustration, the controller may be implemented by one or more programmable processors 508. The device may also include a display interface 510 to output data for the user interface as previously discussed (e.g., pressure delivery parameter settings, questions, prompts, respiratory pathology indicators, etc.) to a display such as on a monitor, LCD panel, touch screen, etc. A user control/input interface 512, for example, for a keyboard, touch panel, control buttons, mouse etc. may also be included as previously discussed and for inputting data, or otherwise activating or operating the methodologies described herein. The device may also include a sensor or data interface 514, such as a bus, for receiving/transmitting data such as programming instructions, indicators, settings data and other output or input of the previously described algorithms.

The device also includes memory/data storage components 520 containing control instructions and data of the aforementioned methodologies. For example, at 522, they may include stored processor control instructions for the user interface and related methodologies such as prompting for input, selection and modification of parameter settings and pathology indicators etc. At 524, these may also include stored processor control instructions for respiratory treatment control such as feedback processing and pressure control adjustment according to the selected pressure delivery settings, etc. Finally, they may also include stored data at 526 for the methodologies such as sets of pressure delivery parameter settings, respiratory pathology indicators, indicators and settings associations, queries or prompts, tables or other data structures, input selections, input adjustments, etc.

In some embodiments, the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

In the foregoing description and in the accompanying drawings, specific terminology and drawing symbols are set forth to provide a thorough understanding of the present technology. In some instances, the terminology and symbols may imply specific details that are not required to practice the technology. For example, while some steps of the methodologies have been described in certain order it will be understood that other ordering and parallel processing of the steps may also be implemented. Moreover, although the technology herein has been described with reference to particular embodiments, it is to be understood that these embodiments are merely illustrative of the principles and applications of the technology. It is therefore to be understood that numerous modifications may be made to the illustrative embodiments.

For example, while in some embodiments the setup procedures previously described may operate in a respiratory treatment apparatus so as to automate selection of the settings for that particular apparatus, in some embodiments, the set-up procedures may be implemented on a set-up apparatus, such as a general purpose computer or special purpose processing device. Upon completion of the set-up methodologies described herein, the selected settings may then be communicatively transferred to a respiratory treatment apparatus 102 from the set-up apparatus, for example, by wired or wireless data communication. The respiratory treatment apparatus 102 may then utilize the settings chosen by the set-up apparatus for the control of the pressure treatment provided by the respiratory treatment apparatus.

Other arrangements may be devised without departing from the spirit and scope of the technology.

The invention claimed is:

1. A method for using a processor to control a delivery of a flow of breathable gas by a respiratory treatment apparatus, the method comprising:

using the processor for storing in a memory an association of arrays of pressure delivery parameter settings with a plurality of respiratory pathology indicators, the plurality of respiratory pathology indicators representing different names of respiratory diseases;

using the processor for prompting for an input associated with at least one of the plurality of respiratory pathology indicators;

using the processor for receiving input indicating a particular one of the plurality of respiratory pathology indicators; and in a procedure of the processor to set control of the delivery of the flow of breathable gas by the respiratory treatment apparatus, in response to the received input, selecting and setting an array of pressure delivery parameter settings associated with the particular one of the plurality of respiratory pathology indicators for the respiratory treatment apparatus to control the delivery of the flow of breathable gas according to the array of pressure delivery parameter settings.

2. The method of claim 1 wherein a respiratory pathology indicator of the plurality of respiratory pathology indicators represents obstructive disorder.

3. The method of claim 1 wherein a respiratory pathology indicator of the plurality of respiratory pathology indicators represents restrictive disorder.

4. The method of claim 1 wherein a respiratory pathology indicator of the plurality of respiratory pathology indicators represents Chronic Obstructive Pulmonary Disease.

5. The method of claim 1 wherein a respiratory pathology indicator of the plurality of respiratory pathology indicators represents obesity hypoventilation syndrome.

6. The method of claim 1 wherein an array of pressure delivery parameter settings of the arrays of pressure delivery parameter settings comprises at least two of a rise time setting, an inspiratory time to respiration cycle time ratio setting, a cycling sensitivity setting, a trigger sensitivity setting, a positive end expiratory pressure setting, a pressure support setting, a maximum pressure support setting and a minimum pressure support setting.

7. The method of claim 1 wherein an array of pressure delivery parameter settings of the arrays of pressure delivery parameter settings comprises initial settings that are modifiable by further operation of the processor.

8. The method of claim 1 further comprising prompting for input of classification information concerning the respiratory disease represented by the particular one of the plurality of respiratory pathology indicators.

9. The method of claim 8 wherein the classification information comprises a plurality of degrees of severity, and wherein each degree of severity is associated with a different setting for a common pressure delivery parameter.

10. The method of claim 9 wherein the plurality of degrees of severity comprise mild, moderate and severe obstructive disorder.

11. The method of claim 1 further comprising prompting for input of a measured quantification concerning the respiratory disease represented by the particular one of the plurality of respiratory pathology indicators.

12. The method of claim 11 wherein the measured quantification comprises a sniff nasal pressure, and wherein a trigger sensitivity setting is set as a function of the input sniff nasal pressure.

13. The method of claim 11 wherein the measured quantification comprises a height and weight or a body mass index, and wherein an expiratory positive airway pressure setting is set as a function of the input height and weight or the input body mass index.

14. The method of claim 1 further comprising generating a controlled flow of breathable gas according to the selected array of pressure delivery parameter settings associated with the particular one of the plurality of respiratory pathology indicators.

15. The method of claim 1 further comprising prompting for a manual adjustment to the selected array of pressure delivery parameter settings associated with the particular one of the respiratory pathology indicators.

16. An automated parameter-setting respiratory treatment apparatus for delivering a controlled flow of breathable gas, the apparatus comprising:
   a controller having at least one processor to access data representing associations between arrays of pressure delivery parameter settings and a plurality of respiratory pathology indicators, the plurality of respiratory pathology indicators representing different names of respiratory diseases;
   the controller being further configured (a) to prompt for an input associated with at least one of the plurality of respiratory pathology indicators; (b) to receive input indicating a particular one of the plurality of respiratory pathology indicators; and (c) in response to the received input, to select and set an array of pressure delivery parameter settings associated with the particular one of the plurality of respiratory pathology indicators to control flow of breathable gas.

17. The apparatus of claim 16 wherein a respiratory pathology indicator of the plurality of respiratory pathology indicators represents obstructive disorder.

18. The apparatus of claim 16 wherein a respiratory pathology indicator of the plurality of respiratory pathology indicators represents restrictive disorder.

19. The apparatus of claim 16 wherein a respiratory pathology indicator of the plurality of respiratory pathology indicators represents Chronic Obstructive Pulmonary Disease.

20. The apparatus of claim 16 wherein a respiratory pathology indicator of the plurality of respiratory pathology indicators represents obesity hypoventilation syndrome.

21. The apparatus of claim 16 wherein an array of pressure delivery parameter settings of the arrays of pressure delivery parameter settings comprises at least two of a rise time setting, an inspiratory time to respiration cycle time ratio setting, a cycling sensitivity setting, a trigger sensitivity setting, an expiratory positive airway pressure setting, a pressure support setting, a maximum pressure support setting and a minimum pressure support setting.

22. The apparatus of claim 16 wherein an array of pressure delivery parameter settings of the arrays of pressure delivery parameter settings comprises initial settings that are modifiable by further operation of the processor.

23. The apparatus of claim 16 wherein the controller is further configured to prompt for input of classification information concerning the respiratory disease represented by the particular one of the plurality of respiratory pathology indicators.

24. The apparatus of claim 23 wherein the classification information comprises a plurality of degrees of severity, and wherein each degree of severity is associated with a different setting for a common pressure delivery parameter.

25. The apparatus of claim 24 wherein the plurality of degrees of severity comprise mild, moderate and severe obstructive disorder.

26. The apparatus of claim 16 wherein the controller is further configured to prompt for input of a measured quantification concerning the respiratory disease represented by the particular one of the plurality of respiratory pathology indicators.

27. The apparatus of claim 26 wherein the measured quantification comprises a sniff nasal pressure, and wherein a trigger sensitivity setting is set as a function of the input sniff nasal pressure.

28. The apparatus of claim 26 wherein the measured quantification comprises a height and weight or a body mass index, and wherein an expiratory positive airway pressure setting is set as a function of the input height and weight or the input body mass index.

29. The apparatus of claim 16 further comprising a flow generator controlled by the controller, and wherein the controller is further configured to deliver a controlled flow of breathable gas with the flow generator according to the selected array of pressure delivery parameter settings associated with the particular one of the plurality of respiratory pathology indicators.

30. The apparatus of claim 29 wherein the controller is further configured to prompt for a manual adjustment to the selected array of pressure delivery parameter settings associated with the particular one of the plurality of respiratory pathology indicators.

31. An electronic system for automated parameter-setting of a respiratory treatment apparatus for delivering a controlled flow of breathable gas, the system comprising:
   arrays of pressure delivery parameter settings with a plurality of respiratory pathology indicators, the plurality of respiratory pathology indicators representing different names of respiratory diseases;
   processing means for prompting for an input associated with at least one of the plurality of respiratory pathology indicators;
   processing means for receiving input indicating a particular one of the plurality of respiratory pathology indicators; and
   processing means for selecting and setting in response to the received input, an array of pressure delivery parameter settings associated with the particular one of the plurality of respiratory pathology indicators for a respiratory treatment apparatus to deliver a controlled flow of breathable gas.

32. The system of claim 31 further comprising flow generation means for generating a flow of breathable gas based on the selected array of pressure delivery parameter settings associated with the particular one of the plurality of respiratory pathology indicators.

33. The system of claim 32 further comprising means for manual adjustment to the selected array of pressure delivery parameter settings associated with the particular one of the plurality of respiratory pathology indicators.

* * * * *